(12) United States Patent
Kasparian et al.

(10) Patent No.: US 8,514,378 B2
(45) Date of Patent: Aug. 20, 2013

(54) METHOD OF OPTICAL TELEDETECTION OF COMPOUNDS IN A MEDIUM

(75) Inventors: Jérôme Kasparian, Collonges Sous Saleve (FR); Jean-Pierre Wolf, Geneva (FR)

(73) Assignees: Universite Claude Bernard Lyon I, Villeurbanne Cedex (FR); Centre National de la Recherche Scientifique, Paris Cedex (FR)

( * ) Notice: Subject to any disclaimer, the term of this patent is extended or adjusted under 35 U.S.C. 154(b) by 578 days.

(21) Appl. No.: 12/602,245

(22) PCT Filed: May 26, 2008

(86) PCT No.: PCT/FR2008/050903
§ 371 (c)(1),
(2), (4) Date: Jun. 21, 2010

(87) PCT Pub. No.: WO2008/152286
PCT Pub. Date: Dec. 18, 2008

(65) Prior Publication Data
US 2010/0283992 A1    Nov. 11, 2010

(30) Foreign Application Priority Data
May 29, 2007    (FR) ..................... 07 55300

(51) Int. Cl.
*G01J 3/00*    (2006.01)
*G01J 3/40*    (2006.01)

(52) U.S. Cl.
USPC .......................................... 356/51; 356/303

(58) Field of Classification Search
USPC .......................................................... 356/51
See application file for complete search history.

(56) References Cited

U.S. PATENT DOCUMENTS

| | | | |
|---|---|---|---|
| 4,563,585 A | 1/1986 | Ward | |
| 6,122,042 A * | 9/2000 | Wunderman et al. | ........... 356/73 |
| 6,650,810 B1 | 11/2003 | Liebermann et al. | |
| 2002/0057431 A1 | 5/2002 | Fateley et al. | |

FOREIGN PATENT DOCUMENTS

WO    86/01295 A1    2/1986

OTHER PUBLICATIONS

H. Wille et al., "Teramobile: A mobile femtosecond-terawatt laser and detection system", Eur. Phys. J. AP 20, 183-190 (2002).
R. Judson et al., "Teaching Lasers to Control Molecules" Physical Review Letters, vol. 68, No. 10, Mar. 9, 1992, pp. 1500-1503.
T. Baeck et al., "An Overview of Evolutionary Algorithms for Parameter Optimization", Evolutionary Composition 1(1): 1-23, copyright 1993 The Massachusetts Institute of Technology.
J. Kasparian et al., "White-Light Filaments for Atmospheric Analysis", Science vol. 301, Jul. 4, 2003, pp. 61-64.

* cited by examiner

*Primary Examiner* — Roy M Punnoose
(74) *Attorney, Agent, or Firm* — Clark & Brody (57) ABSTRACT

A method and device for optical teledetection of compounds in a medium includes a detection measurement carried out by emitting into the medium, short pulses of light at least 3 nm wide, and detecting a part of the light back-scattered by the medium by means of a detection unit with temporal resolution. A reference measurement in which the light emitted or the light back-scattered is filtered by virtue of addressable filters, simulating the optical spectrum of the light at the working wavelengths of at least one given compound to be searched for. A comparison of the detection and reference measurements is made to deduce therefrom the possible presence of the compound or compound(s) searched for in the medium. The addressable filters are modified dynamically, and a series of reference measurements and corresponding comparisons are performed for a series of various compounds liable to be present in the medium.

26 Claims, 4 Drawing Sheets

Figure 4

METHOD OF OPTICAL TELEDETECTION OF COMPOUNDS IN A MEDIUM

This is a national stage application based on PCT application no. PCT/FR2008/05093 filed on May 26, 2008, which is based on French priority application no. 0755300, filed on May 29, 2007.

FIELD OF THE INVENTION

The invention relates to the technical field of remote detection, more particularly adapted to the detection of aerosols or pollutants in the atmosphere.

BACKGROUND ART

The LIDAR (Light Detection and Ranging) technique is conventionally used for detecting and measuring the concentration of a given gas. Lidar may also be used for detecting liquid or solid particles in suspension in the atmosphere or further for detecting compounds dissolved in a liquid. Lidar consists of sending laser pulses into the medium of interest and of measuring their back-scattering versus time. The fact that the laser is pulsed enables detection as a function of time t and therefore of the distance z between the laser and the measuring point ($z=c \cdot t/2$, c being light velocity in the medium).

Remote detection by Lidar of compounds is often carried out by the DIAL technique in which a pair of close wavelengths is used, respectively adjusted on an absorption band of the compound to be detected and immediately nearby (differential absorption). This technique is only applicable to compounds having at least one fine absorption line in a range where no other potentially present compound has an absorption band. Indeed, it is sensitive to the interferences of other compounds which absorb in the same range of wavelengths. Moreover, depending on the ranges of wavelengths, it may be difficult to produce a tunable monochromatic source adapted to the measurement.

When the spectrum of the compound to be measured does not allow application of the DIAL technique, correlation spectroscopy may be applied. Correlation spectroscopy consists of using a light source with great spectral width, modulated upon crossing a reference sample containing the compound to be measured. But this technique lacks flexibility since, for each measurement, the adapted reference has to be available. Further, the intensity intended to be absorbed by the compound to be measured is pre-attenuated in the reference sample. In order to obtain a sufficient measured signal, it is therefore necessary to have an intense light source, which may pose eye safety problems both for the operators and for the general public.

SUMMARY OF THE INVENTION

In this context, the invention proposes to provide a novel method and a novel device for detecting pollutants in a medium, which are easy to apply and which allow detection of the presence of a large number of pollutants.

The method must also have high detection sensitivity and be adapted to the determination of the concentration of the detected compound(s).

The method must also meet the requirements in terms of eye safety.

The present invention relates to a method for remote optical detection of compounds in a medium in which:

a detection measurement is conducted by emitting into the medium, from a light source, called a detection light source, short light pulses with a width of at least 3 nm, preferably of at least 10 nm, and detecting a portion of the back-scattered light from the medium by means of a detection unit with temporal resolution, a reference measurement is conducted by emitting into the medium, from a light source, called a reference light source, with characteristics identical with the detection light source, short light pulses into the medium, and detecting a portion of the back-scattered light from the medium by means of a detection unit with temporal resolution, the emitted light or the back-scattered light being filtered by means of addressable filtering means, simulating the optical spectrum of the light at the working wavelengths of at least one given compound to be sought, comparing a detection measurement and a reference measurement, in order to infer therefrom the possible presence of the sought compound(s) in the medium, the addressable filtering means are modified dynamically, and a series of reference measurements and a series of corresponding comparisons are conducted for a series of different compounds likely to be present in the medium.

The object of the invention is also a device for remote optical detection of compounds in a medium, which comprises:

a series of components for a detection measurement, comprising a light source, called a detection light source, emitting into the medium short light pulses covering a wide band of wavelengths with a width of at least 3 nm, preferably with a width of at least 10 nm, and with a temporal resolution detection unit for a portion of the back-scattered light from the medium, delivering a detection measurement, a series of components for a reference measurement, comprising a light source, called reference light source, with characteristics identical with the detection light source, emitting short light pulses into the medium, addressable filtering means which filter the emitted light or the back-scattered light, and simulate the optical spectrum of the light at the working wavelengths of at least one given compound to be sought, and a unit with temporal resolution for detecting a portion of the back-scattered light from the medium, delivering a reference measurement, means for comparing a detection measurement and a reference measurement, in order to infer therefrom the possible presence of the sought compound(s) in the medium, and automated means for modifying the addressable filtering means with which a series of reference measurements may be conducted for a series of different compounds likely to be present in the medium.

The method and the device according to the invention are particularly suitable for remote detection of gas compounds, such as atmospheric pollutants in a gas medium. It is also possible to apply the method according to the invention for detecting solid or liquid particles or aerosols in a gaseous medium, or further compounds dissolved in a liquid medium. The detection in a liquid medium such as water for example is of interest for detecting pollutants in the sea bed.

BRIEF DESCRIPTION OF THE DRAWINGS

With the description which follows, with reference to the appended figures, the invention may be better understood.

DETAILED DESCRIPTION OF THE INVENTION

Within the scope of the invention, pulses covering a large band of wavelengths are used, which will allow determination of the possible presence of wide range of compounds. The pulses preferably have a width of at least 3 nm, preferably at least 10 nm. Preferably these pulses are white light pulses. Conventionally, by white light is meant a continuous polychromatic light signal covering a spectrum of wavelengths of at least 100 nm in width.

As examples of white light sources, mention may be made of arc lamps, incandescent lamps, or any other analogous device. According to an alternative embodiment, the detection light source and the reference light source comprise a laser delivering light pulses, for which the wavelength spectrum is widened. It is generally possible to use a laser diode. For example, in the case of a monochromatic laser delivering intense pulses, notably with a power above 3 GW, phase self-modulation occurs in the atmosphere according to the principle of the self-guided filament (J. Kasparian et al., Science, 2003, 301, 61). This filament is produced when ultra-short and high power pulses typically of more than 3 GW in air, modify the refractive index of air on their path, this change in refractive index leading in return to self-focusing and to guiding of the beam on a light filament. A spontaneous widening of the spectrum of wavelengths and of white light pulses from a laser source with intense pulses is thereby obtained. In this case, the light source does not directly deliver white light pulses but monochromatic pulses, which become polychromatic during their propagation, and this before reaching the medium of interest. The white light source may also be an intense laser, the wavelength spectrum of which is widened, for example by phase self-modulation or by the Raman effect in a cell such as a gas, water cell or a cell of any other non-linear medium. In this case, the cell may be directly placed at the output of the laser. As an intense laser, mention may be made of solid lasers of the Nd:YAG type. According to an alternative embodiment, the detection light source and the reference light source deliver pulses with a duration from 20 fs to 10 ps, preferably from 100 fs to 300 fs, and preferably, with a power from 3 GW to 100 TW, preferably from 0.5 TW to 5 TW.

The detection light source and the reference light source have the same characteristics, in terms of pulse duration, power and spectral range. The detection light source may be distinct from the reference light source. It is also possible that the detection measurement(s) and the reference measurement(s) be conducted with a single light source, the detection measurement being then conducted without any filtering. In this case, the filtering means may be modified sequentially and rapidly, in order to alternate the detection measurements and the reference measurements, and thus to get rid of errors due to possible fluctuations of the level of the light source and/or of the medium.

Generally, it is preferable to conduct a new detection measurement for each reference measurement, for example by alternating or conducting simultaneously detection and reference measurements as detailed hereafter, in order to carry out the comparison between two measurements conducted closely in time. The device may then include control means providing alternation of the detection measurement and reference measurement.

However, it is not excluded that different reference measurements should be compared with a same detection measurement or else that a new detection measurement used for the comparison should be conducted periodically after a series of reference measurements.

The addressable filtering means may comprise an optical spatial phase and/or amplitude modulator, or a reflective or interferential microelectronic system or any other analogous device. The filtering means simulate the optical spectrum of the light at the working wavelengths of at least one given compound. The filtering means are periodically modified automatically so as to successively simulate for different compounds their optical light spectrum at their working wavelengths. In the sense of the invention, when filtering occurs on the emitted light, the optical spectrum of the light at the working wavelengths corresponds to the optical spectrum of the light emitted at the wavelengths which are weakly absorbed or preferably at the wavelengths which are strongly absorbed by one or more given compounds. By weakly absorbed wavelengths, are notably meant, wavelengths for which, for a given compound, an attenuation of at most 10% of the light intensity, is observed over the whole of the path covered by the light, during the measurement. By strongly absorbed wavelengths, are notably meant wavelengths for which, for a given compound, an attenuation of at least 30% of the light intensity is observed over the whole of the path covered by the light during the measurement.

It is possible that the reference and detection measurements be conducted so as to detect linear or non-linear phenomena. In the case of linear phenomena, there is coincidence between the emitted wavelength in the medium and the back-scattered wavelength. On the other hand, in the case of non-linear phenomena, notably observed in the case of intense pulses, for example with a power of more than 1 GW, modification of the back-scattered wavelength relatively to the emitted wavelength is observed. When filtering occurs on the back-scattered light, there again, in the case of measuring linear phenomena, the optical light spectrum at the working wavelengths may correspond to the spectrum of the back-scattered light at wavelengths which are weakly absorbed or preferably at wavelengths which are strongly absorbed by one or more given compounds to be sought. On the other hand, in the case when non-linear phenomena are detected, the spectrum of the back-scattered light at the working wavelengths corresponds to the spectrum of the back-scattered light at the wavelengths back-scattered by the sought compound which differs from the spectrum of the light emitted at wavelengths which are weakly or strongly absorbed by the sought compound. Given that the reference measurement only corresponds to the light signal which is back-scattered at the wavelengths which are weakly or strongly absorbed by one or more given compounds, it is possible to increase the power of the emitted light corresponding to these wavelengths over the medium, in order to increase the sensitivity of the system. As the power of the back-scattered light is limited, it is easier to observe the eye safety standards.

The filtering means are modified automatically in order to successively simulate the spectra at working wavelengths of a series of different compounds. The filtering means may for example include different filters positioned on a filter holder. Motorized displacement means of the filters ensure selection of the desired filter. It is also possible, and this in a preferred way, that the different spectra characteristic of the compounds be stored in a spectroscopic database, to which are connected the filtering means through control means.

It is also possible that the filtering means be adapted for simulating certain conditions such as temperature, pressure, speed, direction of the wind, possessed by the medium into which the pulses are emitted.

Within the scope of the invention, a detection unit comprises means for detecting at least one portion of the back-scattered photons. Collecting means, such as a telescope, may be positioned in front of the detection means. With these collecting means, it is notably possible to increase the signal detected by the detection means from the back-scattered light. The detection means are generally associated with acquisition and processing means which acquire and utilize the signals delivered by the detection means. For example, the received photons are converted into photoelectrons, the corresponding electric signal is in direct relationship with absorption of the radiation and with the gas molecules to be analyzed, by applying the Beer-Lambert law. Given that the emitted light is in the form of pulses and that the detection means detect the signal as a function of time, it is possible to determine at which distance is found the medium which back-scatters the detected photons. It is then possible to calculate the distribution of the concentrations along the shooting axis of the light source, up to a limit defined as being the range of the source.

As detection means adapted for applying the invention, mention may be made of photomultipliers, photodiodes or any other analogous device. The detection means used with temporal resolution, allow the evolution of the detected signal to be recorded over time. Preferably, the temporal resolution of the detection means if very fine, for example of less than 10 ns. As stated earlier, the detection means integrate means for spatially resolving the signal with which it is possible to determine at which distance is located the medium which backscatters the detected light. Spatial resolution is obtained by means of the temporal resolution of the detection means. The detected signal may thus be correlated with the emission distance of the medium which emits it. Preferably, the spatial resolution of the detection means is less than 1 meter. The acquisition of the signal is most often carried out over a reduced period of time.

At the detection unit, it is possible to select the means for processing the signal, so as to modulate the processing of the signal. For example, the signal obtained during reference measurements, may be adjusted and/or optimized by a closed loop algorithm so as to be adapted to the measured concentration at the previous iteration. Adaptation of the transmission for each wavelength section or spectral component, may thus be modulated independently, via a multi-parameter optimization algorithm, such as a genetic algorithm in which the optimum solution, i.e. the synthetic spectrum which is the closest to the species to be detected, is obtained by trial and error, the attempts giving a favorable result being combined in order to produce the optimum solutions (cf. T. Back, H. Schwefel, *An Overview of evolutionary algorithms for parameter optimization*, Evolutionary computing 1, 1 (1993) and R. S. Judson and H. Rabitz, Teaching lasers to control molecules, Physical Review Letters, 68, 1500 (1992)).

It is possible that the detection and reference measurements be conducted with a single detection unit or with two distinct detection units.

Advantageously, the measurements and the comparison are carried out so as to determine the concentration of the detected present compound. For this, the comparison is carried out with processing means and means for computing the concentration of the detected compound which for example, apply algorithms analogous to those used in LIDAR or DIAL techniques or in correlation spectroscopy. For example, the computation methods used are derived from those used for the DIAL technique (Differential Absorption Lidar, see for example R. M. Measures, *Laser remote sensing—Fundamentals and applications*, 1984, New York: Wiley Interscience).

If a species or a compound is considered for which the absorption cross-section integrated over the light spectrum of the reference source is $\sigma_R$, and the absorption cross-section integrated over the light spectrum of the measuring source is $\sigma_m$, then the concentration (expressed in molecules per unit volume) of this species at a distance z is:

$$N(z) = \frac{1}{2 \cdot (\sigma_M - \sigma_R)} \cdot \frac{d}{dz}\left(\ln\left(\frac{S_R}{S_M}\right)\right)$$

wherein $S_M(z)$ and $S_R(z)$ respectively represent the signal measured on the measurement and reference detector respectively.

In the case when the comparison is carried out between total light and the weakly absorbed wavelengths, or between the strongly absorbed wavelengths and the weakly absorbed wavelengths, this formula may be directly applied.

In the case when the comparison is carried out between the total light $S_M$ and the weakly absorbed wavelength $S_R$, the cross-sections $\sigma_R$ and $\sigma_m$ are practically equal. In order to ensure mathematical stability of the method, the auxiliary value $S'_m = S_M - S_R$, will then be used, for which the absorption cross-section is $\sigma'_R = \sigma_M - \sigma_R \approx 0$. The concentration of the sought species is then $$N(z) = \frac{1}{2 \cdot (\sigma'_M - \sigma_R)} \cdot \frac{d}{dz}\left(\ln\left(\frac{S_R}{S'_M}\right)\right)$$

In the case when the filtering means simulate the light spectrum at the working wavelengths of several compounds of interest simultaneously, the calculation of the mixture ratios may be carried out by a closed loop optimization or by any analogous algorithm.

According to a first alternative, the addressable filtering means are placed between the light source used for the reference measurement and the medium, so as to filter the emitted light during the reference measurement. The filtering means for example comprise an optical spatial phase and/or amplitude modulator or a reflective or interferential microelectronic system.

According to a second alternative, the addressable filtering means are placed between the medium and the detection means used for the reference measurement, so as to filter the back-scattered light, during the reference measurement. In order to carry out such filtering, the filtering means notably comprise means with which the wavelengths which are strongly absorbed by compound(s) to be detected may be oriented towards a detection unit and the wavelengths which are weakly absorbed by the compound(s) to be detected may be oriented towards another detection unit, the detection and reference measurements then be carried out simultaneously.

Figure 1:
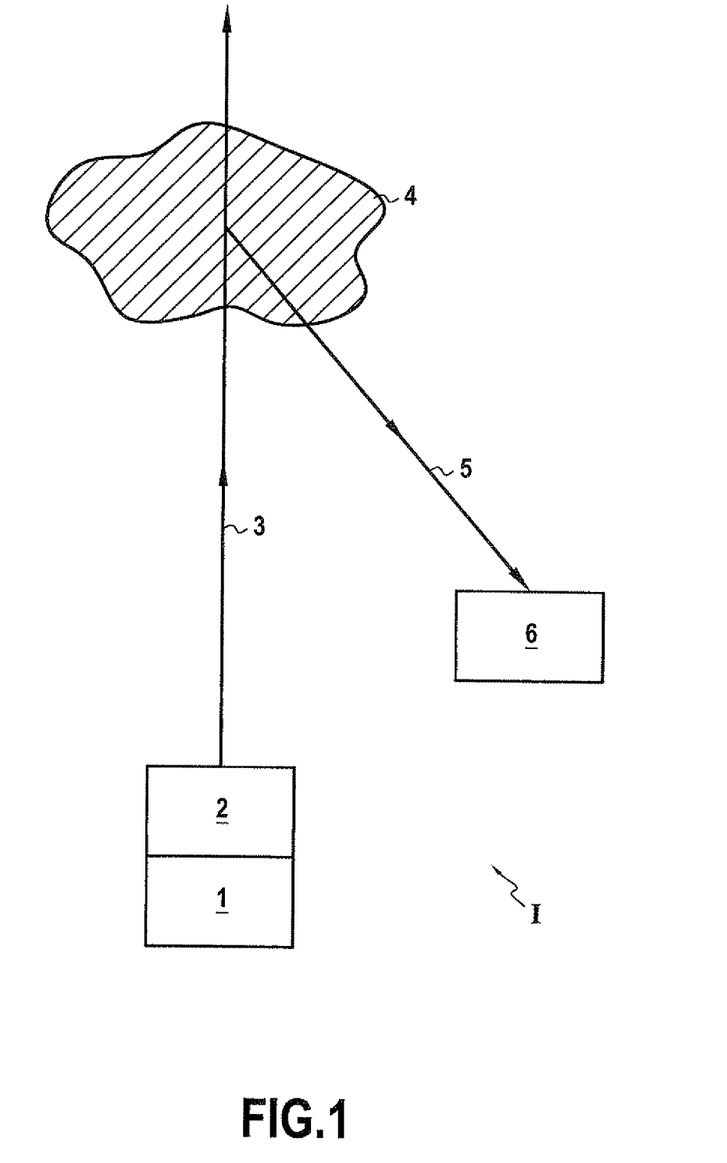
FIG. 1 schematically illustrates an alternative of the device according to the invention in which the filtering means are located upstream from the medium of interest.

The first alternative of the invention above is notably illustrated in FIG. 1. The device I comprises a single light source 1 used for the detection measurement(s) and the reference measurements. Filtering means 2 are placed at the output of the light source 1, between the light source used for the reference measurement and the gas medium in order to filter the emitted light during the reference measurement. During a reference measurement, these filtering means 2 filter the light emitted by the source 1, in order to allow emission of only certain wavelengths which correspond to the wavelengths strongly absorbed by one or more compounds to be detected. During a detection measurement, the filtering means are disabled. The emitted light 3 in the form of short pulses propagates towards the gas medium 4 of interest. A portion of the back-scattered light 5 is detected by a detection unit 6 including detection means with temporal resolution. The intensity difference between detection measurement conducted in the absence of filtering and the reference measurement conducted with filtering is directly proportional to the concentration of the sought compound(s). According to an alternative operation, the filtering means allow emission not of strongly absorbed wavelengths but of weakly absorbed wavelengths towards the medium.

Such an alternative embodiment in which the filtering means are positioned upstream from the gas medium allows a reduction in the power of the emitted light which is then reduced to the wavelengths for which back-scattering is observed with the compound of interest. In this case, it is easier to observe the standards of eye safety.

The second alternative of the invention mentioned earlier is, for example illustrated in FIG. 2. The device II comprises a single light source 11 used for the detection measurement(s) and the reference measurements. The light 12 as short pulses emitted by the light source 11 propagates towards the gas medium 13 of interest. A portion of the back-scattered light 14 is detected by a detection unit 15 including detection means with temporal resolution, upstream from which filtering means 16 are placed. During a reference measurement, these filtering means 16 filter the light back-scattered by the gas medium 13, so that only certain wavelengths, which correspond to the strongly (or weakly) absorbed wavelengths by one or more compounds to be detected, are directed towards the detection unit 15. During a detection measurement, the filtering means are disabled. The intensity difference between the detection measurement conducted in the absence of filtering and the reference measurement conducted with filtering is directly proportional to the concentration of the sought compound(s).

Figure 2:
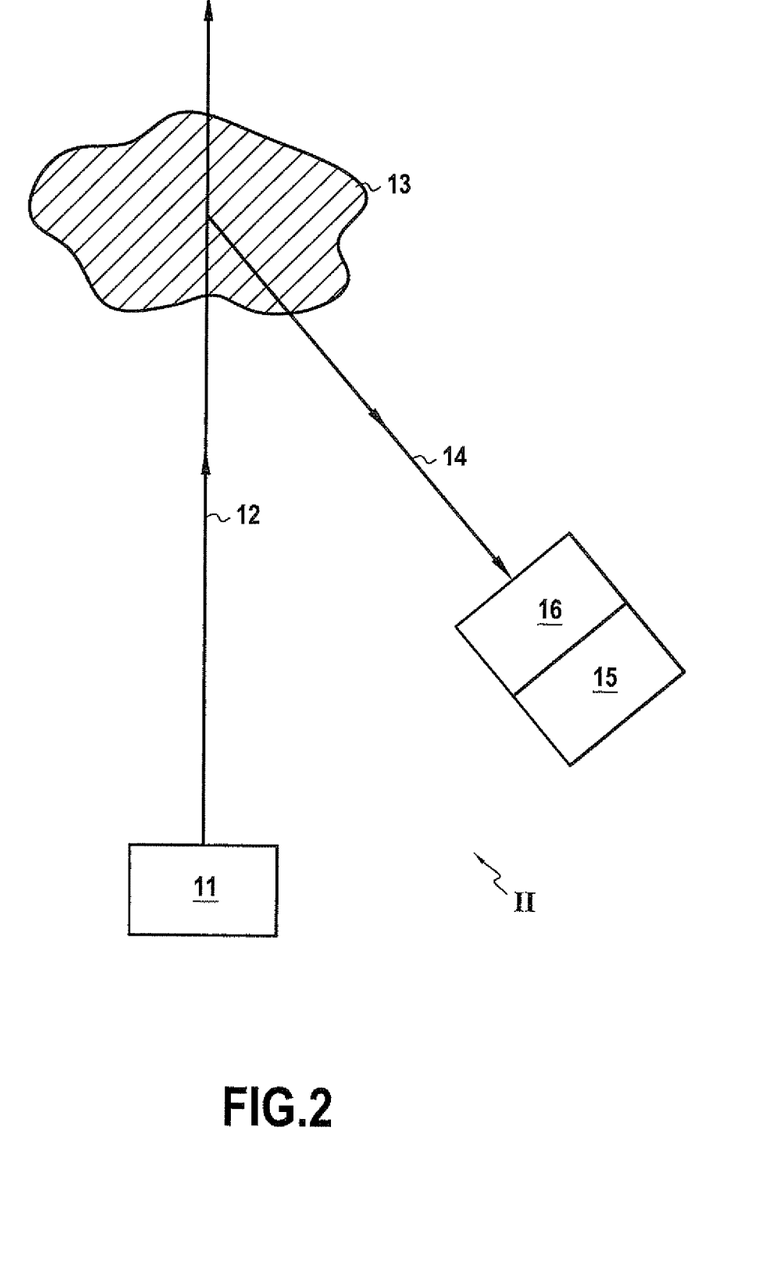
FIGS. 2 and 3 schematically illustrate two different alternatives of a device according to the invention in which the filtering means are located downstream from the medium of interest.

In this alternative, the filtering means only receive the light back-scattered by the medium and not the totality of the light emitted by the reference light source. Therefore the risks of aging or deterioration of the filter are reduced.

Figure 3:
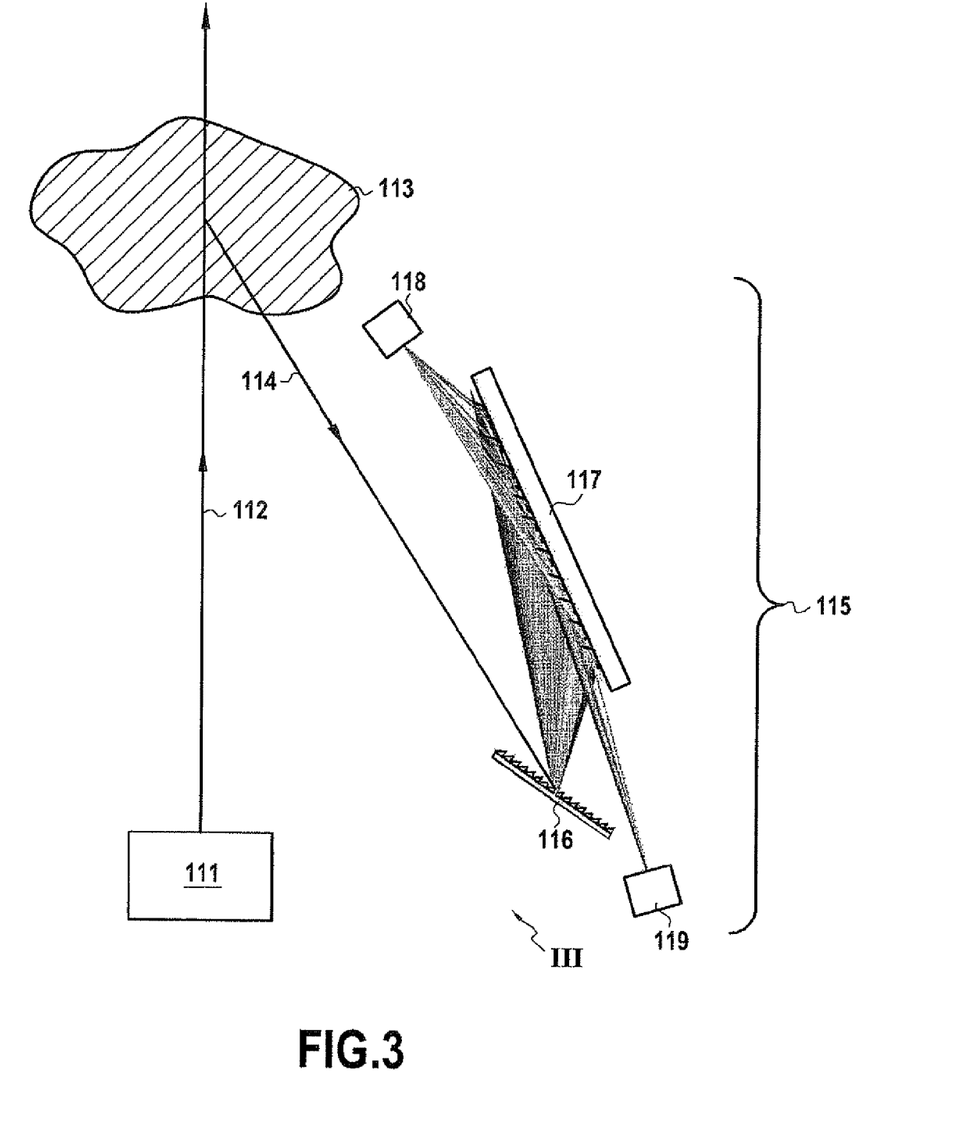

FIG. 3 illustrates another alternative in which the addressable filtering means are placed between the gas medium and the detection unit used for the reference measurement and the detection measurement, so as to filter the back-scattered light, upon simultaneous taking of the reference measurement and of the detection measurement. In FIG. 3, the device III comprises a single light source 111 used for the detection measurement(s) and the reference measurements. The light 112 as short pulses emitted by the light source 111 propagates towards the gas medium 113 of interest. A portion of the back-scattered light 114 is filtered by filtering means 115 placed downstream from the gas medium 113 which comprise means for orienting the wavelengths strongly absorbed by the compound(s) to be detected towards a detection unit and orienting the wavelengths weakly absorbed by the compound(s) to be detected towards another detection unit. In FIG. 3, the filtering means 115 comprise light dispersion means 116 such as a prism and means 117 for reflecting the obtained dispersed light which orient the light beam, depending on its wavelength, towards either one of the detection units 118 and 119. The filtering means 115 have been voluntarily illustrated at a large scale in order to facilitate understanding. In reality, the detection means are located at a distance from the medium of interest which may attain several kilometers. The reflection means 117 may be a micro-electromechanical device such as a network of micro-mirrors mounted on piezo-electric actuators, or any other reflective device, each element of which may be oriented independently and rapidly with a control signal.

The detection unit 118 receives the wavelengths which are weakly absorbed by the compound to be measured and allows the detection (or reference) measurement to be conducted. The detection unit 119 receives the wavelengths strongly absorbed by the compound to be measured and allows the reference (or detection respectively) measurement to be conducted. According to calculation techniques used in the DIAL differential absorption techniques, it is possible to measure the concentration of the compound of interest. Thus, the reference and detection measurements are conducted simultaneously, with which it is possible to get rid of the fluctuations which may occur in the medium between two successive measurements.

In this case, the reference measurement and the detection measurement are conducted simultaneously. The detection measurement for example corresponds to the measurement conducted with the detection means which receive the wavelengths which are weakly absorbed (called $\lambda_{off}$) by the gas compound(s) to be detected and the reference measurement corresponds to the one conducted with the detection means which receive the wavelengths which are strongly absorbed (called $\lambda_{on}$) by the gas compound(s) to be detected, or vice versa. The calculation methods with which it is possible to obtain the concentration of the gas compound to be detected are well-known to one skilled in the art, and notably correspond to those used in the DIAL differential absorption technique.

Figure 4:
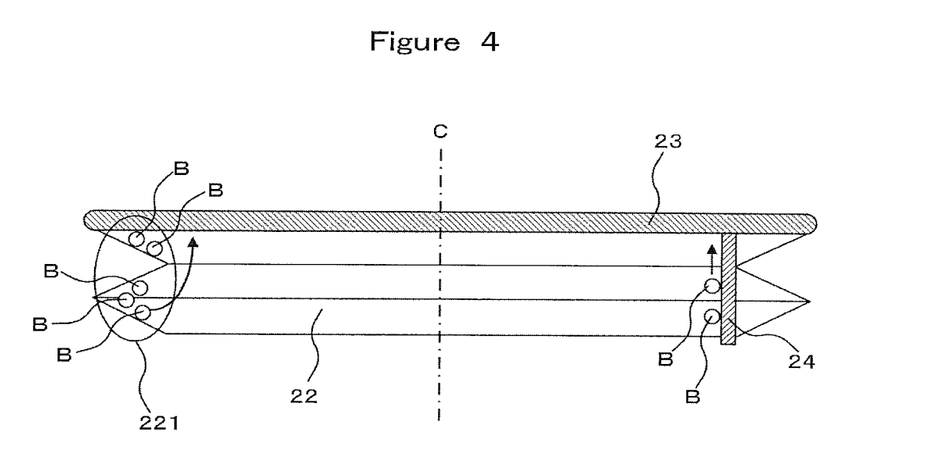
FIG. 4 schematically illustrates another alternative of a device according to the invention comprising two distinct light sources, one used for the detection measurements, the other one for the reference measurements.

The device IV described in FIG. 4 comprises two light sources 211 and 212, one used for the detection measurements and the other one for reference measurements. The light 213 alternately emitted by each of these sources, 211 and 212 respectively, follow the same path, the direction of the light beam being modified by means of a device 214 including means for changing the propagation path of the light. Such a device 214 for example appears as a mobile mirror, the orientation of which is alternately modified depending on the light source from which originates the light. At the output of the device 214, the path of the light emitted by the light source 211 coincides with that of the light emitted by the source 212, so that regardless of the light source, the emitted light 213 propagates towards the gas medium 215 of interest, along the same path. A portion of the back-scattered light 216 is detected by a detection unit 217 including detection means with temporal resolution, upstream from which filtering means 218 are placed. During a reference measurement, the filtering means 218 filter light back-scattered by the gas medium 215, so that only certain wavelengths, which correspond to the wavelengths strongly (or weakly) absorbed by one or more compounds to be detected, are directed towards the detection unit 217. During a detection measurement, the filtering means are disabled. The intensity difference between the detection measurement conducted in the absence of filtering, and the reference measurement conducted with filtering is directly proportional to the concentration of the sought compound(s).

The invention claimed is:

1. A method for remote optical detection of compounds in a medium wherein
   a detection measurement is conducted by emitting into the medium from a source of light, called a detection light source, short light pulses covering a wide band of wavelengths with a width of at least 10 nm, and by detecting a portion of the light back-scattered by the medium by means of a unit with temporal resolution,
   a reference measurement is conducted by emitting into the medium, from a source of light, called a reference light source, with characteristics identical with the detection light source, short light pulses into the medium, and by detecting a portion of the light back-scattered by the medium by means of a detection unit with temporal resolution, the emitted light or the back-scattered light being filtered by a addressable filtering means, simulating the optical spectrum of the light at the working wavelengths of at least one given compound to be sought,
   by comparing a detection measurement and a reference measurement, in order to infer therefrom the possible presence of the sought compound(s) in the medium,
   the addressable filtering means are modified dynamically, and a series of reference measurements and a series of corresponding comparisons are carried out for a series of different compounds likely to be present in the medium.

2. The method according to claim 1, characterized in that the detection light source and the reference light source comprise a laser emitting pulses, the wavelength spectrum of which is widened.

3. The method according to claim 1 characterized in that the detection light source and the reference light source deliver pulses with a duration from 20 fs to 10 ps, and with a power from 3 GW to 100 TW.

4. The method according to claim 3 characterized in that the detection light source and the reference light source deliver pulses with a duration from 100 fs to 300 fs.

5. The method according to claim 3 characterized in that the power is from 0.5 TW to 5 TW.

6. The method according to claim 1, characterized in that the pulses emitted into the medium are pulses of white light.

7. The method according to claim 1, characterized in that the measurements and the comparison are carried out so that to determine the concentration of the detected present compound.

8. The method according to claim 1, characterized in that the detection measurement(s) and the reference measurements are conducted with a single light source, the detection measurement being conducted without any filtering.

9. The method according to claim 1, characterized in that a different detection measurement is conducted for each reference measurement.

10. The method according to claim 1, characterized in that the addressable filtering means are placed between the light source used for the reference measurement and the medium, in order to filter the emitted light during the reference measurement.

11. The method according to claim 1, characterized in that the filtering means comprise an optical spatial phase and/or amplitude modulator or a reflective or interferential microelectronic system.

12. The method according to claim 1, characterized in that the addressable filtering means are placed between the medium and the detection unit used for the reference measurement so as to filter the back-scattered light during the reference measurement.

13. The method according to claim 12, characterized in that the filtering means comprise means with which the wavelengths strongly absorbed by the compound(s) to be detected may be oriented towards a detection unit and wavelengths weakly absorbed by the compound(s) to be detected may be oriented towards another detection unit, the detection and reference measurements being then conducted simultaneously.

14. The device for remote optical detection of compounds in a medium which comprises:
   a series of components for a detection measurement, comprising a light source, called a detection light source, emitting into the medium, short pulses of light with a width of at least 10 nm, and a unit for detecting with temporal resolution a portion of the light back-scattered by the medium, delivering a detection measurement,
   a series of components for a reference measurement, comprising a source of light, called a reference light source, with characteristics identical with the detection light source, emitting short pulses of light into the medium, addressable filtering means, which filter the emitted light or the back-scattered light, and simulate the optical spectrum of the light at the working wavelengths of at least one given compound to be sought, and a unit for detecting with temporal resolution a portion of the light back-scattered by the medium, delivering a reference measurement and
   means for comparing a detection measurement and a reference measurement, in order to infer therefrom the possible presence of the sought compound(s) in the medium,
   automated means for modifying the addressable filtering means allowing a series of reference measurement to be conducted for a series of different compounds likely to be present in the medium.

15. The device according to claim 14, characterized in that the detection light source and the reference light source comprise a laser.

16. The device according to claim 14, characterized in that the detection light source and the reference light source emit pulses with a duration from 20 fs to 10 ps, and with a power from 3 GW to 100 TW.

17. The device according to claim 16, characterized in that the detection light source and the reference light source emit pulses with a duration from 100 fs to 300 fs.

18. The device according to claim 16 characterized in that the power is from 0.5 TW to 5 TW.

19. The device according to claim 14, characterized in that the detection units and the comparison means include means for calculating the concentration of the detected present compound(s).

20. The device according to claim 14, characterized in that the detection light source is distinct from the reference light source.

21. The device according to claim 14, characterized in that the detection light source and the reference light source are a single and same light source, the detection measurement being conducted without any filtering.

22. The device according to claim 14, characterized in that it includes control means for alternating a detection measurement and a reference measurement.

23. The device according to claim 14, characterized in that the addressable filtering means are placed between the light source used for the reference medium and the medium, in order to filter the emitted light during the reference measurement.

24. The device according to claim 14, characterized in that the filtering means comprise an optical spatial phase and/or amplitude modulator or a reflective or interferential microelectronic system.

25. The device according to claim 14, characterized in that the addressable filtering means are placed between the medium and the detection unit used for the reference measurement, so as to filter the back-scattered light during the reference measurement.

26. The device according to claim 25, characterized in that the filtering means comprise means with which the wavelengths strongly absorbed by the compound(s) to be detected may be oriented towards a detection unit and the wavelengths weakly absorbed by the compound(s) to be detected may be oriented towards another detection unit, the detection and reference measurements being then conducted simultaneously.

* * * * *

UNITED STATES PATENT AND TRADEMARK OFFICE
CERTIFICATE OF CORRECTION

PATENT NO. : 8,514,378 B2  Page 1 of 1
APPLICATION NO. : 12/602245
DATED : August 20, 2013
INVENTOR(S) : Kasparian et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 783 days.

Signed and Sealed this
Fifteenth Day of September, 2015

Michelle K. Lee
*Director of the United States Patent and Trademark Office*